United States Patent [19]

Meister et al.

[11] Patent Number: 5,747,329
[45] Date of Patent: May 5, 1998

[54] GLUTAMYLCYSTEINE SYNTHETASE LIGHT SUBUNIT

[75] Inventors: Alton Meister; Chin-Shiou Huang; Mary E. Anderson, all of New York, N.Y.

[73] Assignee: Cornell Research Foundation, Inc., Ithaca, N.Y.

[21] Appl. No.: 350,325

[22] Filed: Dec. 5, 1994

Related U.S. Application Data

[63] Continuation of Ser. No. 45,808, Apr. 8, 1993, abandoned, which is a continuation-in-part of Ser. No. 765,211, Sep. 25, 1991, abandoned, which is a continuation of Ser. No. 464,871, Jan. 16, 1990, abandoned.

[51] Int. Cl.$^6$ .............................. C12N 1/20; C12N 9/00; C12D 21/06; C07H 21/04
[52] U.S. Cl. .................. 435/252.33; 435/183; 435/69.1; 435/320.1; 536/23.2; 536/23.5; 536/23.1
[58] Field of Search ................................. 536/23.5, 23.2; 435/252.3, 252.33, 6, 7.6, 69.1, 183

[56] References Cited

PUBLICATIONS

Apontoweil, P., et al., Biochimica et Biophysica Acta 399:1–9 (1975).
Grill, E., et al., Proc Natl Acad Sci USA 86:6838–6842 (1989).
Gushima, H., et al., Agric Biol Chem 47(8):1927–1928 (1983).
Huang, C.S., et al., Proc Natl Acad Sci USA 85:2464–2468 (1988), Apr. 1, 1988.
Lehninger, A.L., in "Biochemistry" 2d Edition, Lehninger, A.L., Worth Publishers, Inc., New York, NY, pp. 98–109 (1975).
Majerus, P.W., et al., The Journal of Clinical Investigation 50:1637–1643 (1971).
Meister, A., in "The Enzymes" 3d Edition, Academic Press, Inc., New York, NY pp. 671–697 (1974).
Meister, A., et al., in "Metabolic Basis of Inherited Diseases", 6th Edition, pp. 855–868 (1989).
Moore, W.R., et al., Proc Natl Acad Sci USA 86:1461–1464 (1989).
Mutoh, N., et al., Biochemical and Biophysical Research Communications 151(1):32–39 (1988).
Ohtake, Y., et al., Agric Biol Chem 52(11):2753–2762 (1988).
Seelig, G.F., et al., The Journal of Biological Chemistry 259(15):9345–9347 (1984).
Seelig, G.F., et al., Mehtods of Enzymology 113:379–390 (1985).
Seelig, G.F., et al., The Journal of Biological Chemistry 259(6):3534–3538 (1984).
Sekura, R., et al., The Journal of Biological Chemistry 252(8):2599–2605 (1977).
Snoke, J.E., et al., The Journal of Biological Chemistry 199:407–414 (1952).
Watanabe, K., et al., Nucleic Acids Research 14(11):4393–4400 (1986).
Yan, N., et al., The Journal of Biological Chemistry 265(3):1588–1593 (1990).
Young, R.A., et al., Proc Natl Acad Sci USA 80:1194–1198 (1983).

*Primary Examiner*—Robert A. Wax
*Assistant Examiner*—Tekchand Saidha
*Attorney, Agent, or Firm*—Pennie & Edmonds LLP

[57] ABSTRACT

The nucleotide cDNA sequence for the light subunit of gamma glutamylcysteine synthetase, and the amino acid sequence for this subunit, are disclosed

40 Claims, 4 Drawing Sheets

GLUTAMYLCYSTEINE SYNTHETASE LIGHT SUBUNIT

The subject application is a continuation of U.S. Ser. No. 08/045,808, filed Apr. 8, 1993, which was a continuation-in-part of U.S. Ser. No. 07/765,211, filed Sep. 25, 1991, which was a continuation of U.S. Ser. No. 07/464,871, filed Jan. 16, 1990, all now abandoned. The contents of each of these applications are incorporated herein by reference.

Partial funding for the making of the invention described herein was provided by the United States National Institutes of Health under Grant No. 4R37 DK12034. Accordingly, the United States Government has certain statutory rights to the claimed invention under 35 USC 200 et seq.

Glutathione is a tripeptide thiol (L-gamma-glutamyl-L-cysteinylglycine) present in animal tissues, plants, and microorganisms. It is found intracellularly in high (0.1 to 10 mM) millimolar concentrations and is thus the most prevalent cellular thiol and the most abundant low molecular weight peptide typically found in mammals. The two characteristic structural features of glutathione—the gamma-glutamyl linkage and a sulfhydryl group—promote its intracellular stability and are intimately associated with its multiple biochemical functions.

Glutathione protects cells from the toxic effects of reactive oxygen compounds and is an important component of the system that uses reduced pyridine nucleotide to provide the cell with its reducing properties which promote, for example, intracellular formation of cysteine and the thiol forms of proteins; glutathione functions in catalysis, metabolism, and transport; it participates in reactions involving the synthesis of proteins and nucleic acids and in those that detoxify free radicals and peroxides; it forms conjugates with a variety of compounds of endogenous and exogenous origin and is a cofactor for various enzymes.

A generalized outline of the biochemistry of glutathione is depicted in the Glutathione cycle schematic appearing in U.S. patent application 765,211, and is incorporated in toto herein.

Glutathione functions as a co-enzyme for formaldehyde dehydrogenase, maleylacetoacetate isomerase, glyoxalase, prostaglandin endoperoxidase isomerases, and dichlorodiphenyltrichloroethane dehydrochlorinase and similar enzymes. In the glyoxalase reaction, the hemimercaptal formed nonenzymatically by reaction of methylglyoxal and glutathione (GSH) is converted by glyoxalase I to S-lactyl-Glutathione, which is split by glyoxalase II to D-lactate and Glutathione. In the formaldehyde dehydrogenase reaction, S-formyl Glutathione is formed (Glutathione+HCHO+ $NAD^+$) and hydrolyzed to formate and Glutathione.

Within cells, GSH is synthesized by the actions of gamma-glutamylcysteine synthetase and Glutathione synthetase as shown in the following reactions. Gamma-glutamylcysteine catalyzes the first of these reactions and is the rate limiting reaction in Glutathione synthesis.

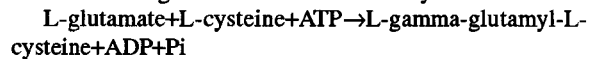
L-glutamate+L-cysteine+ATP→L-gamma-glutamyl-L-cysteine+ADP+Pi

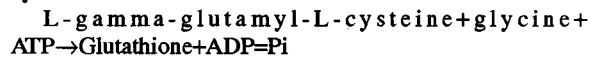
L-gamma-glutamyl-L-cysteine+glycine+ATP→Glutathione+ADP=Pi

Humans who lack either of the two enzymes needed for glutathione synthesis experience a number of serious physical symptoms including mental retardation, hemolytic anemia, and paralyses.

The activity of the holoenzyme is feedback inhibited by GSH [see J. Biol. Chem. 250:1422 (1975)]. Such inhibition, which provides a mechanism that regulates the GSH level in various tissues, is accompanied by reduction of the enzyme and by competitive inhibition by GSH with respect to glutamate [see J. Biol. Chem (1993)].

Highly purified preparations of gamma-glutamylcysteine synthetase have been isolated from several sources including rat erythrocytes, bacteria, and rat kidney. The enzyme purified from rat kidney ($M_r$ approximately 104,000) is homogeneous on gel electrophoresis and dissociates under denaturing conditions to yield two nonidentical subunits—a heavy subunit of $M_r$~73,000 and a light subunit of $M_r$~27,700. The holoenzyme can also be dissociated into two subunits under nondenaturing conditions. The isolated heavy subunit is catalytically active and it is feedback inhibited by GSH. These findings led to cloning and sequencing of the cDNA coding for the heavy subunit described in U.S. patent application 765,211. This open frame oligonucleotide sequence of the heavy subunit is:

| | | | | | | | | | | | | | |
|---|---|---|---|---|---|---|---|---|---|---|---|---|---|
| ATG | GGG | CTG | CTG | TCC | CAA | GGC | TCG | CCA | CTG | AGC | TGG | GAA | 39 |
| GAG | ACC | CAG | CGC | CAC | GCC | GAC | CAC | GTG | CGG | AGA | CAC | GGC | 78 |
| ATC | CTC | CAG | TTC | CTG | CAC | ATC | TAC | CAC | GCA | GTC | AAG | GAC | 117 |
| CGG | CAC | AAG | GAC | GTG | CTC | AAG | TGG | GGT | GAC | GAG | GTG | GAG | 156 |
| TAC | ATG | TTG | GTG | TCC | TTT | GAT | CAT | GAA | AAT | AGG | AAA | GTC | 195 |
| CAG | TTG | TTA | CTG | AAT | GGC | GGC | GAT | GTT | CTT | GAA | ACT | CTG | 234 |
| CAA | GAG | AAG | GGG | GAG | AGG | ACA | AAC | CCC | AAC | CAC | CCA | ACC | 273 |
| CTC | TGG | AGA | CCA | GAG | TAT | GGG | AGT | TAC | ATG | ATT | GAA | GGG | 312 |
| ACA | CCT | GGC | CAG | CCG | TAC | GGA | GGA | ACG | ATG | TCC | GAG | TTC | 351 |
| AAC | ACA | GTG | GAG | GAC | AAC | ATG | AGG | AAA | CGC | CGG | AAG | GAG | 390 |
| GCT | ACT | TCT | GTA | TTA | GGA | GAA | CAT | CAG | GCT | CTT | TCG | ACG | 429 |
| ATA | ACT | TCA | TTT | CCC | AGG | CTA | GGC | TGC | CCT | GGA | TTC | ACA | 468 |
| CTG | CCA | GAG | CAC | AGA | CCC | AAC | CCA | GAG | GAA | GGA | GGT | GCA | 507 |
| TCT | AAG | TCC | CTC | TTC | TTT | CCA | GAC | GAA | GCC | ATA | AAC | AAG | 546 |
| CAC | CCC | CGC | TTT | GGT | ACT | CTA | ACA | AGA | AAC | ATC | CGG | CAT | 585 |
| CGG | AGA | GGA | GAA | AAG | GTT | GTC | ATC | AAT | GTG | CCA | ATA | TTC | 624 |
| AAG | GAC | AAG | AAC | ACA | CCA | TCT | CCG | TTT | GTA | GAA | ACA | TTT | 663 |
| CCT | GAG | GAT | GAG | GAG | GCA | TCA | AAG | GCC | TCT | AAG | CCA | GAC | 702 |
| CAC | ATC | TAC | ATG | GAT | GCC | ATG | GGA | TTT | GGG | ATG | GGC | AAC | 741 |
| TGC | TGT | CTT | CAG | GTG | ACA | TTC | CAA | GCC | TGC | AGT | ATA | TCT | 780 |
| GAG | GCA | AGA | TAC | CTT | TAT | GAC | CAG | TTG | GCC | ACT | ATC | TGC | 819 |
| CCA | ATT | GTT | ATG | GCT | TTG | AGT | GCT | GCA | TCG | CCA | TTT | TAC | 858 |
| CGA | GGC | TAC | GTG | TCA | GAC | ATT | GAT | TGT | CGC | TCG | GGA | GTG | 897 |
| ATT | TCT | GCA | TCT | GTA | GAT | GAT | AGA | ACA | CGG | GAG | GAG | AGA | 936 |
| GGA | CTG | GAG | CCC | CTG | AAG | AAC | AAT | CGC | TTT | AAA | ATC | AGT | 975 |
| AAG | TCT | CGG | TAT | GAC | TCA | ATA | GAT | AGC | TAC | CTG | TCC | AAG | 1014 |

-continued

| | | | | | | | | | | | | | |
|---|---|---|---|---|---|---|---|---|---|---|---|---|---|
| TGT | GGA | GAG | AAG | TAC | AAT | GAC | ATC | GAC | CTG | ACC | ATC | GAC | 1053 |
| ACG | GAG | ATC | TAC | GAG | CAG | CTC | TAA | GAG | GAA | GGC | ATC | GAT | 1092 |
| CAC | CTT | CTG | GCA | CAG | CAG | GTT | GCT | CAT | CTC | TTT | ATT | AGA | 1131 |
| GAC | CCA | CTG | ACC | CTT | TTT | GAA | GAG | AAA | ATT | CAT | CTG | GAT | 1170 |
| GAT | GCC | AAC | GAG | TCT | GAC | CAT | TTT | GAG | AAT | ATT | CAG | TCC | 1209 |
| ACA | AAC | TGG | CAG | ACA | ATG | AGG | TTT | AAG | CCT | CCT | CCT | CCA | 1248 |
| AAC | TCA | GAT | ATT | GGA | TGG | AGA | GTA | GAG | TTC | CGA | CCA | ATG | 1287 |
| GAG | GTA | CAG | TTG | ACA | GAC | TTT | GAG | AAC | TCT | GCC | TAT | GTG | 1326 |
| GTA | TTT | GTG | GTA | CTG | CTG | ACC | AGG | GTG | ATC | CTC | TCA | TAC | 1365 |
| AAA | CTA | GAC | TTC | CTC | ATT | CCA | CTG | TCC | AAG | GTT | GAC | GAG | 1404 |
| AAC | ATG | AAA | GTG | GCA | CAG | GAG | CGA | GAT | GCC | GTC | TTA | CAG | 1443 |
| GGG | ATG | TTT | TAT | TTC | AGG | AAA | GAC | ATT | TGC | AAA | GGT | GGC | 1482 |
| AAC | GCC | GTG | GTG | GAT | GGG | TGT | AGC | AAG | GCC | CAG | ACC | AGC | 1521 |
| TCC | GAG | CCA | TCT | GCA | GAG | GAG | TAC | ACG | CTC | ATG | AGC | ATA | 1560 |
| GAC | ACC | ATC | ATC | AAT | GGG | AAG | GAA | GGC | GTG | TTT | CCT | GGA | 1599 |
| CTC | ATC | CCC | ATT | CTG | AAC | TCC | TAC | CTT | GAA | AAC | ATG | GAA | 1638 |
| GTC | GAC | GTG | GAC | ACC | CGA | TGC | AGT | ATT | CTG | AAC | TAC | CTG | 1677 |
| AAG | CTA | ATT | AAG | AAG | AGA | GCA | TCT | GGA | GAA | CTA | ATG | ACT | 1716 |
| GTT | GCC | AGG | TGG | ATG | AGA | GAG | TTT | ATT | GCA | AAC | CAT | CCT | 1755 |
| GAC | TAC | AAG | CAA | GAC | AGT | GTA | ATA | ACT | GAT | GAG | ATC | AAC | 1794 |
| TAT | AGC | CTC | ATT | TTG | AAA | TGC | AAT | CAA | ATT | GCA | AAT | GAA | 1833 |
| TTG | TGT | GAA | TGT | CCA | GAG | TTA | CTT | GGA | TCA | GGC | TTT | AGA | 1872 |
| AAA | GCG | AAG | TAC | AGT | GGA | GGT | AAA | AGC | GAC | CCT | TCA | GAC | 1911 |
| TAG | 1914 | | | | | | | | | | | | |

This open reading frame translates into the peptide:

| | | | | | | | | | | | | | |
|---|---|---|---|---|---|---|---|---|---|---|---|---|---|
| Met | Gly | Leu | Leu | Ser 5 | Gln | Gly | Ser | Pro | Leu 10 | Ser | Trp | Glu | Glu | Thr 15 |
| Gln | Arg | His | Ala | Asp 20 | His | Val | Arg | Arg | His 25 | Gly | Ile | Leu | Gln | Phe 30 |
| Leu | His | Ile | Tyr | His 35 | Ala | Val | Lys | Asp | Arg 40 | His | Lys | Asp | Val | Leu 45 |
| Lys | Trp | Gly | Asp | Glu 50 | Val | Glu | Tyr | Met | Leu 55 | Val | Ser | Phe | Asp | His 60 |
| Glu | Asn | Arg | Lys | Val 65 | Gln | Leu | Leu | Leu | Asn 70 | Gly | Gly | Asp | Val | Leu 75 |
| Glu | Thr | Leu | Gln | Glu 80 | Lys | Gly | Glu | Arg | Thr 85 | Asn | Pro | Asn | His | Pro 90 |
| Thr | Leu | Trp | Arg | Pro 95 | Glu | Tyr | Gly | Ser | Tyr 100 | Met | Ile | Glu | Gly | Thr 105 |
| Pro | Gly | Gln | Pro | Tyr 110 | Gly | Gly | Thr | Met | Ser 115 | Glu | Phe | Asn | Thr | Val 120 |
| Gly | Glu | His | Gln | Ala 125 | Leu | Cys | Thr | Ile | Thr 130 | Ser | Phe | Pro | Arg | Leu 135 |
| Gly | Glu | His | Gln | Ala 140 | Leu | Cys | Thr | Ile | Thr 145 | Ser | Phe | Pro | Arg | Leu 150 |
| Gly | Cys | Pro | Gly | Phe 155 | Thr | Leu | Pro | Glu | His 160 | Arg | Pro | Asn | Pro | Glu 165 |
| Glu | Gly | Gly | Ala | Ser 170 | Lys | Ser | Leu | Phe | Phe 175 | Pro | Asp | Glu | Ala | Ile 180 |
| Asn | Lys | His | Pro | Arg 185 | Phe | Gly | Thr | Leu | Thr 190 | Arg | Asn | Ile | Arg | His 195 |
| Arg | Arg | Gly | Glu | Lys 200 | Val | Val | Ile | Asn | Val 205 | Pro | Ile | Phe | Lys | Asp 210 |
| Lys | Asn | Thr | Pro | Ser 215 | Pro | Phe | Val | Glu | Thr 220 | Phe | Pro | Glu | Asp | Glu 225 |
| Glu | Ala | Ser | Lys | Ala 230 | Ser | Lys | Pro | Asp | His 235 | Ile | Tyr | Met | Asp | Ala 240 |
| Met | Gly | Phe | Gly | Met 245 | Gly | Asn | Cys | Cys | Leu 250 | Gln | Val | Thr | Phe | Gln 255 |
| Ala | Cys | Ser | Ile | Ser 260 | Glu | Ala | Arg | Tyr | Leu 265 | Tyr | Asp | Gln | Leu | Ala 270 |
| Thr | Ile | Cys | Pro | Ile 275 | Val | Met | Ala | Leu | Ser 280 | Ala | Ala | Ser | Pro | Phe 285 |
| Tyr | Arg | Gly | Tyr | Val 290 | Ser | Asp | Ile | Asp | Cys 295 | Arg | Trp | Gly | Val | Ile 300 |
| Ser | Ala | Ser | Val | Asp 305 | Asp | Arg | Thr | Arg | Glu 310 | Glu | Arg | Gly | Leu | Glu 315 |
| Pro | Leu | Lys | Asn | Asn 320 | Arg | Phe | Lys | Ile | Ser 325 | Lys | Ser | Arg | Tyr | Asp 330 |
| Ser | Ile | Asp | Ser | Tyr 335 | Leu | Ser | Lys | Cys | Gly 340 | Glu | Lys | Tyr | Asn | Asp 345 |
| Ile | Asp | Leu | Thr | Ile 350 | Asp | Thr | Glu | Ile | Tyr 355 | Glu | Gln | Leu | Leu | Glu 360 |
| Glu | Gly | Ile | Asp | His | Leu | Leu | Ala | Gln | His | Val | Ala | His | Leu | Phe |

-continued

| | | | | 365 | | | | | 370 | | | | | 375 |
|---|---|---|---|---|---|---|---|---|---|---|---|---|---|---|
| Ile | Arg | Asp | Pro | Leu | Thr | Leu | Phe | Glu | Glu | Lys | Ile | His | Leu | Asp |
| | | | | 380 | | | | | 385 | | | | | 390 |
| Asp | Ala | Asn | Glu | Ser | Asp | His | Phe | Glu | Asn | Ile | Gln | Ser | Thr | Asn |
| | | | | 395 | | | | | 400 | | | | | 405 |
| Trp | Gln | Thr | Met | Arg | Phe | Lys | Pro | Pro | Pro | Pro | Asn | Ser | Asp | Ile |
| | | | | 410 | | | | | 415 | | | | | 420 |
| Gly | Trp | Arg | Val | Glu | Phe | Arg | Pro | Met | Glu | Val | Gln | Leu | Thr | Asp |
| | | | | 425 | | | | | 430 | | | | | 435 |
| Phe | Glu | Asn | Ser | Ala | Tyr | Val | Val | Phe | Val | Val | Leu | Leu | Thr | Arg |
| | | | | 440 | | | | | 445 | | | | | 450 |
| Val | Ile | Leu | Ser | Tyr | Lys | Leu | Asp | Phe | Leu | Ile | Pro | Leu | Ser | Lys |
| | | | | 455 | | | | | 460 | | | | | 465 |
| Val | Asp | Glu | Asn | Met | Lys | Val | Ala | Gln | Glu | Arg | Asp | Ala | Val | Leu |
| | | | | 470 | | | | | 475 | | | | | 480 |
| Gln | Gly | Met | Phe | Tyr | Phe | Arg | Lys | Asp | Ile | Cys | Lys | Gly | Gly | Asn |
| | | | | 485 | | | | | 490 | | | | | 495 |
| Ala | Val | Val | Asp | Gly | Cys | Ser | Lys | Ala | Gln | Thr | Ser | Ser | Glu | Pro |
| | | | | 500 | | | | | 505 | | | | | 510 |
| Ser | Ala | Glu | Glu | Tyr | Thr | Leu | Met | Ser | Ile | Asp | Thr | Ile | Ile | Asn |
| | | | | 515 | | | | | 520 | | | | | 525 |
| Gly | Lys | Glu | Gly | Val | Phe | Pro | Gly | Leu | Ile | Pro | Ile | Leu | Asn | Ser |
| | | | | 530 | | | | | 535 | | | | | 540 |
| Tyr | Leu | Glu | Asn | Met | Glu | Val | Asp | Val | Asp | Thr | Arg | Cys | Ser | Ile |
| | | | | 545 | | | | | 550 | | | | | 555 |
| Leu | Asn | Tyr | Leu | Lys | Leu | Ile | Lys | Lys | Arg | Ala | Ser | Gly | Glu | Leu |
| | | | | 560 | | | | | 565 | | | | | 570 |
| Met | Thr | Val | Ala | Arg | Trp | Met | Arg | Glu | Phe | Ile | Ala | Asn | His | Pro |
| | | | | 575 | | | | | 580 | | | | | 585 |
| Asp | Tyr | Lys | Gln | Asp | Ser | Val | Ile | Thr | Asp | Glu | Ile | Asn | Tyr | Ser |
| | | | | 590 | | | | | 595 | | | | | 600 |
| Leu | Ile | Leu | Lys | Cys | Asn | Gln | Ile | Ala | Asn | Glu | Leu | Cys | Glu | Cys |
| | | | | 605 | | | | | 610 | | | | | 615 |
| Pro | Glu | Leu | Leu | Gly | Ser | Gly | Phe | Arg | Lys | Ala | Lys | Tyr | Ser | Gly |
| | | | | 620 | | | | | 625 | | | | | 630 |
| Gly | Lys | Ser | Asp | Pro | Ser | Asp | | | | | | | | |
| | | | | 635 | | | | | | | | | | |

The recombinant heavy subunit obtained by expression of the cDNA in E. coli (as well as the heavy subunit isolated from the isolated holoenzyme) exhibits a much higher $K_m$ value for glutamate and a greater sensitivity to feedback inhibition by GSH than the holoenzyme. These results suggested to us that the light subunit, although not enzymatically active by itself, may be essential for the enzyme to maintain high affinity for glutamate and appropriate sensitivity to feedback inhibition by GSH.

One aspect of the present invention is to describe the isolation and sequencing of the cDNA coding for the light subunit of γ- glutamylcysteine synthetase.

Another aspect of the present invention is to describe the amino acid sequence of the light subunit of γ- glutamylcysteine synthetase.

Another aspect of the present invention is to describe the cDNA nucleotide sequence for the expression of the light subunit of γ- glutamylcysteine synthetase.

The light subunit of γ-glutamylcysteine synthetase cDNA according to the present invention has been expressed in E. coli, and the catalytic properties of the reconstituted recombinant holoenzyme obtained by co-expression of the light and heavy subunits, and by mixing the separately expressed subunits have been examined.

These and other aspects and findings of the present invention, including elucidation of the nucleotide and amino acid sequences of the light subunit of gamma-glutamylcysteine synthetase will be understood more fully by reference to the following examples, figures, and detailed description.

In the figures.

EXAMPLE I

Figure 1:
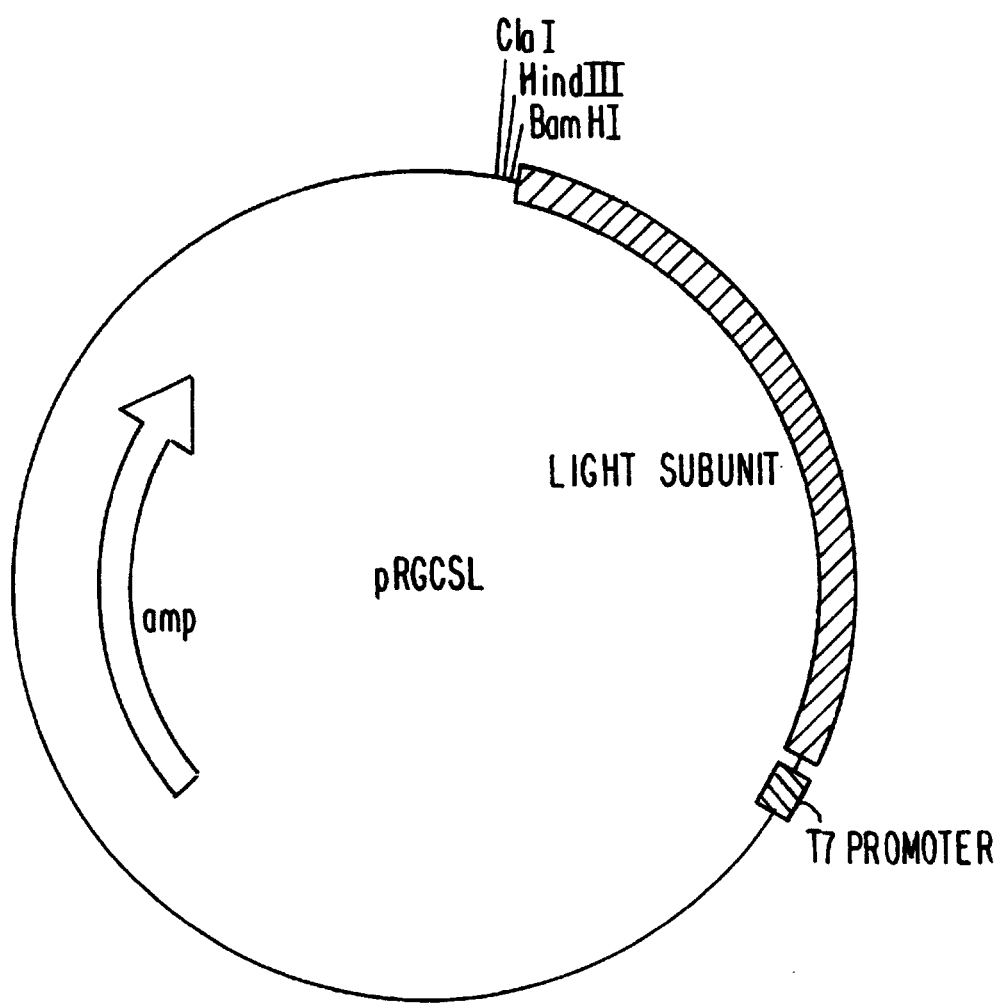
FIG. 1 represents the light subunit expression plasmid, pRGCSL, according to the present invention.

Isolation of antibodies to rat kidney γ-GCS light subunit was conducted as follows:

Rabbit antiserum to the rat holoenzyme [see J. Biol. Chem. 265:1588 (1990)] (5 ml) was applied to a Sepharose 4B (Pharmacia) column containing the recombinant heavy subunit coupled to Sepharose (1 ml) a flow rate of 15 ml/hr; the effluent was recycled through the column for 2 hr. After washing with PBS (10 ml), the light subunit antibodies were eluted from the column with 0.1M glycine (pH 2.5). Fractions (2 ml) were collected into tubes containing 0.1 ml of 1M sodium phosphate (pH 8.0). The specificity of the purified antibody was examined by Western blot analysis, and upon examination it showed a band that reacted with antibody at a molecular weight of approximately 30,000. This antibody so produced was used further in the present invention to screen the cDNA library.

EXAMPLE II

Isolation of the rat kidney γGCS light subunit according to the present invention was conducted as follows:

Purified rat kidney γ-glutamylcysteine synthetase (1 mg, 10 nmole) [see Methods in Enzymology 113:379 (1985)]

was dissolved in 0.5 ml of Tris-HCl buffer (0.5 Ml; pH 8.5) containing 6M guanidinium-HCl and 2 mM EDTA. After bubbling the protein solution with nitrogen gas to avoid oxidation by air, dithiothreitol (1.2 mg, 8 μmole) was added and the reaction mixture was incubated at 55° C. for 4 hr. The solution was then cooled to room temperature and reacted with iodoacetic acid (3 mg, 16 μmole) for 20 min. The reduced and carboxymethylated protein was applied to a C-4 reverse phase HPLC column (4.2×250 mm) equilibrated with 70% solvent A (0.1% trifluoroacetic acid (aqueous) and 30% solvent B (95% acetonitrile, 0.1% trifluoroacetic acid (aqueous). The subunits were separated by a linear gradient of 30 to 70% solvent B, over 40 min, at a flow rate of 1 ml per min and monitored spectrophotometrically at 215 nm.

Figure 4:
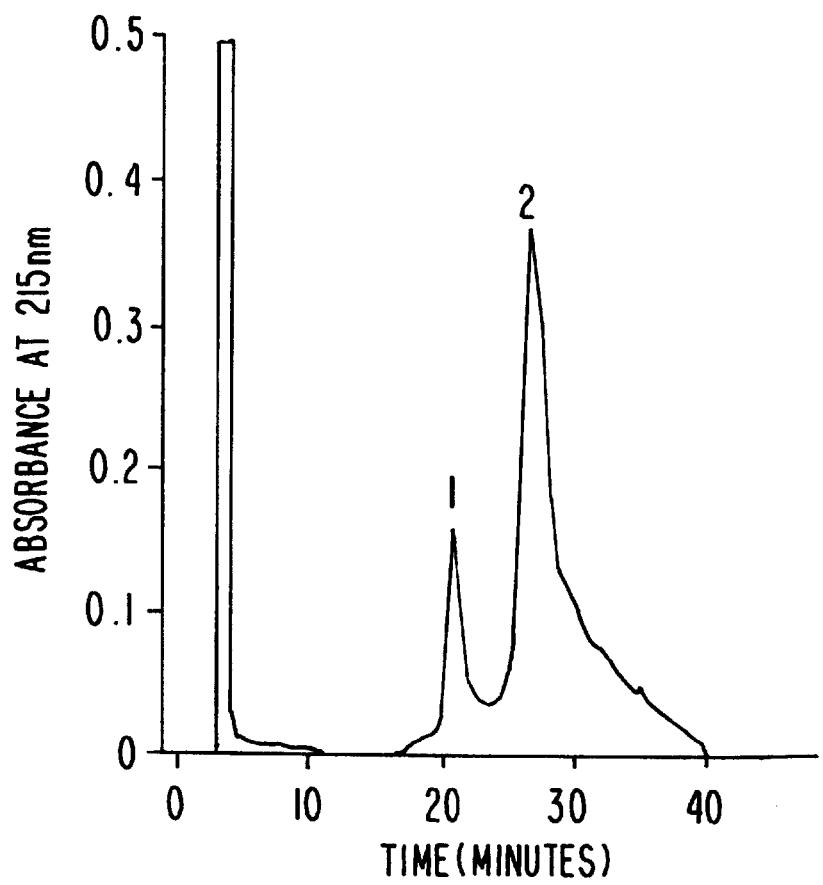
FIG. 4 represents a tracing showing 2 peaks of the separated light and heavy subunits according to the present invention.

As described, the reduced and carboxymethylated holoenzyme were applied to a HPLC C-4 reverse phase column which resulted in two separate protein peaks being eluted from the column (FIG. 4). Peaks 1 and 2 were identified by SDS gel electrophoresis as the light subunit and the heavy subunit, respectively: The purified light subunit was subjected to cleavage with trypsin as described in the following example.

EXAMPLE III

Peptide sequence analysis of rat kidney γGCS light subunit was conducted as follows:

The purified light subunit (0.2 mg) was dissolved in 0.1 ml of Tris-HCl buffer (50 mM; pH 8.0) and reacted with trypsin (6 ng) at 37° C. for 16 hr. The peptides formed were separated by HPLC using a C-18 reverse phase column (4.2×250 mm); a 0% to 70% linear gradient was used, over 70 min, between 0.1% trifluoroacetic acid and 0.01% trifluoroacetic acid containing 95% acetonitrile at a flow rate of 1 ml per min. Automated Edman degradation was carried out with a gas-phase sequencer (Applied Biosystems) equipped with an on-line Phenylthiohydantoin (PTH) amino acid analyzer.

As described above, the peptides according to the present invention were separated by a HPLC C-18 reverse column, and the sequence of two apparently homogeneous peptides were obtained by automatic Edman degradation method. The amino acid sequence of the peptides obtained from the light subunit of γ-glutamylcysteine synthetase are given below:

| Peptide I | Phe | Gln | Glu | Ala | Leu | Gln | Glu |
|---|---|---|---|---|---|---|---|
| mRNA | UUU | CAA | GAA | GCU | CUU | CAA | GAA |
|  | C | G | G | C | U C | G | G |
|  |  |  |  | A | A |  |  |
|  |  |  |  | G | G |  |  |
| Probe | TTT | CAA | GAA | GCI | CTI | CAA | GA |
|  | C | G | G |  | T | G |  |
| Determined sequence | TCC | CAG | GAA | TCT | CTT | CAA | GA |

EXAMPLE IV

Isolation of the cDNA clones for the light subunit of rat kidney γGCS was carried out as follows:

A rat kidney cDNA expression library (Clontech), having an average insert size of 1.1 kb (range from 0.6 to 3.8 kb) and 1.2×10⁶ independent clones in vector λgtII, was immunoscreened as described by Sambrook [see J. Sambrook, E. f. Fritsch and T. Maniatis, "Molecular Cloning, a Laboratory Manual" Cold Spring Harbor Laboratory Press (1989)] using antibody, prepared in accordance with Example I, to the light subunit. An overnight culture of *E. coli* Y1090r- (Clontech) grown in LB medium containing 0.2% maltose and 10 mM MgSO₄, was divided into ten 0.1 ml portions. Each tube containing a portion was infected with 5×10⁴ plaque formation units (pfu) of the bacteriophage λgtII expression library (Clontech) at 37° C. for 15 min. After mixing with 7 ml of top agarose (LB medium containing 0.75% agarose), the infected bacteria were poured onto 10 LB agar plates (150×35 mm) containing ampicillin (100 μg/ml) and incubated at 42° C. for 3.5 hr. The plates were then covered with isopropylthiogalactoside (IPTG) (10 mM)-treated nitrocellulose filters, and incubated at 37° C. for 4 hrs. The filters were carefully peeled off the plates and rinsed with TNT Buffer (10 mM Tris-HCl (pH 8.0), 150 mM NaCl, and 0.05% Tween 20). The plates were then covered with second set of nitrocellulose filters and incubated at 37° C. for an additional 6 hrs.

The two sets of nitrocellulose filters were treated with blocking buffer (TNT containing 5% nonfat dry milk) for 1 hr followed by the same buffer containing diluted (1:500) antibody to the light subunit for an additional 4 hrs. After washing with TNT Buffer three times, the filters were treated with diluted (1:5000) peroxidase-linked goat anti-rabbit IgG antibody for 1 hr. After washing (five times), the antigen- Peptide I:

| Glu | Leu | Leu | Ser | Glu | Ala | Ser | Phe | Gln | Glu | Ala | Leu | Gln | Glu | Ser |
|---|---|---|---|---|---|---|---|---|---|---|---|---|---|---|
|  |  |  |  | 5 |  |  |  |  | 10 |  |  |  |  | 15 |
| Ile | Pro | Asp | Ile | Glu | Ala | Gln | Glu |  |  |  |  |  |  |  |
|  |  |  |  | 20 |  |  |  |  |  |  |  |  |  |  |

Peptide II:

| Ser | Leu | Glu | His | Leu | Gln | Pro | Tyr | Xaa | Glu | Glu | Leu | Glu | Asn | Leu |
|---|---|---|---|---|---|---|---|---|---|---|---|---|---|---|
|  |  |  |  | 5 |  |  |  |  | 10 |  |  |  |  | 15 |
| Val | Gln | Ser |  |  |  |  |  |  |  |  |  |  |  |  |

An oligonucleotide probe was designed and synthesized corresponding to the sequence deduced from peptide I. The probe is a mixture of 32 different 20-mer oligonucleotides corresponding to all codons combination derived from peptide I, above. The letter I in the sequence below represents deoxyinosine, and has been substituted at the wobble positions in two of the codons.

antibody complex was detected by incubating the filters with Tris-HCl buffer (10 mM; pH 7.5) containing 0.018% H₂O₂ and 0.06% 3,3'-diaminobenzidine for 5 min. Positive plaques that appeared on both sets of the nitrocellulose filters were picked, grown and re-screened with the same antibody.

As described, a rat kidney cDNA λgtII expression library, containing the cDNAs in the phage EcoRI site, was screened with antibody to the light subunit. From about 5×10⁵ phages, 38 positive clones were obtained. The expressed fusion protein from 21 of those clones reacted with the antibody when tested by western blot analysis. The phage DNA from those clones were isolated, and the two clones (numbered 62 and 71) with the largest inserts were chosen for further analysis. When digested with EcoRI followed by agarose gel electrophoresis, two DNA bands that represent the insert cDNAs were obtained from each of the two clones. Thus, clone 62 was found to contain a 1 kb and a 0.4 kb band, while a 0.7 and a 0.4 kb bands were found contained in clone 71. These results indicate that the cDNAs in these two clones most likely contains similar DNA sequences. Southern blot analysis showed that the 1 kb band from clone 62 and the 0.7 kb band from clone 71 hybridized with the oligonucleotide probe described above. It was the #1.0, 0.7, and 0.4 kb DNAs that were subcloned into the ECoRI site of phagmid pBluescript KS–(+) for sequence analysis.

EXAMPLE V

Purification of recombinant bacteriophage λDNA was conducted as follows:

Recombinant λphage particles (1×10⁶ pfu), obtained from the positive clones, were separately incubated with *E. coli* Y1090r- (1×10⁸ cells) at 37° C. for 20 min. The infected cells were inoculated in 50 ml of prewarmed LB medium until the cells lysed (about 6–8 hrs). After removal of cellular debris by centrifugation (3000×g for 5 min), the λphage was precipitated by adding NaCl (2.9 g) and polyethylene glycol (MW 8000; 5 g) to the medium. After standing on ice for 2 hrs, the precipitated phage particles were recovered by centrifugation (5000×g for 10 min). The pellet was resuspended with 4 ml of TM buffer (50 mM Tris-HCl (pH 7.5) and 10 mM MgSO₄); and the excess PEG8000 was removed by extracting the solution with 4 ml of chloroform. The aqueous layer was passed through a DE52 column (4 ml) pre-equilibrated with TM buffer. The column was washed with 3 ml of TM and the effluent (7 ml) was collected. Isopropanol (7 ml) and NaCl (400 #1; 4M) were added to the effluent and the solution was placed on ice for 1 hr. The phage was precipitated by centrifugation (8000×g for 10 min) and resuspended with 500 µl TE buffer (10 mM Tris-HCl; pH 8.0, and 1 mM EDTA). The phage solution was extracted with 500 µl phenol (saturated with Tris-HCl buffer, pH 8.0), followed by extraction with the same volume of phenol/chloroform (1:1). This extraction by phenol and phenol/chloroform was repeated several times until no precipitate appeared at the interface of the extraction. The solution was then extracted with chloroform and the DNA was precipitated with 40 µl 0.3M sodium acetate and 1 ml of ethanol.

EXAMPLE VI

Southern blot analysis of the recombinant DNA was conducted as follows:

Recombinant λgtII DNA (3 g) from Example 5 was digested with EcoR I and the resulting fragments were separated by agarose (0.8%) gel electrophoresis. The digested DNA was transferred by capillary action to a Nitran membrane filter in 10×SSPE Buffer (20×SSPE: 3M NaCl, 0.2M NaH₂PO₄, and 20 mM EDTA). The filter was incubated at 45° C. for 3 hr in prehybridization buffer [6×SSPE, 5×Denhardt's solution (0.1% Ficoll 400, 0.1% polyvinylpyrrolidone, 0.1% bovine serum albumin, 0.5% SDS, and 100 µg/ml denatured and fragmented salmon sperm DNA) followed by incubation at 45° C. overnight in the same buffer containing ³²P-labeled oligonucleotide probe (2×10⁵ cpm; 10⁹ cpm/µg). The probe was synthesized according to the sequence deduced from the peptide sequence obtained from tryptic digestion of the light subunit. The filter was washed with 2×SSPE containing 0.5% SDS for 5 min at room temperature followed by washing with 1×SSPE 30 min at 45° C. Autoradiography was performed at room temperature overnight.

EXAMPLE VII

DNA sequence analysis of the DNA according to the present invention was performed as follows:

The inserts of the recombinant λgtII phage DNA were excised by treatment with EcoRI, and isolated from agarose gel and purified using a Geneclean™ kit in accordance with the manufacture's instructions. The cDNAs were subcloned into the EcoRI site of the phagemid pBluescript KS-(+) (Strategene). The nucleotide sequence was determined on either pBluescript single or double stranded DNA by dideoxynucleotide chain termination method [see Proc. Natl. Acad. Sci. USA 74:5463 (1977)] using Sequenase (U.S. Biochemicals) according to the manufacturer's instructions. T7, SK primers, as well as the primers corresponding to internal light subunit sequence were used. Sequence analysis was performed using PC/Gene software.

The cDNA sequence of the light subunit was derived, as described above, from the cDNA inserts of the recombinant clone 62 and 71. The entire positive strand was sequenced at least three times from different overlapping sets using internal primers. The sequence was confirmed by sequencing the complementary strand twice.

The cDNA sequence corresponding to the light subunit of γ-glutamylcysteine synthetase mRNA is presented below:

| | | | | | | | | | | | | |
|---|---|---|---|---|---|---|---|---|---|---|---|---|
| GAATTCCGGC | CTTCCCTCCG | TGGCTCCGGC | GCTGCCCGGT | CCCCTCGGGC | | | | | | | | 50 |
| GGCAGCTGCC | 60 | | | | | | | | | | | |
| ATG | GGC | ACC | GAC | AGC | CGC | GCG | GCC | GGA | GCA | CTT | CTG | GCG | 99 |
| CGG | GCC | AGC | ACC | CTG | CAC | CTG | CAG | ACC | GGG | AAC | CTG | CTC | 138 |
| AAC | TGG | GGC | CGC | CTG | CGG | AAA | AAG | TGT | CCG | TCC | ACG | CAC | 177 |
| AGC | GAG | GAG | CTT | CGA | GAC | TGT | ATC | CAA | AAG | ACC | TTG | AAT | 216 |
| GAA | TGG | AGC | TCC | CAA | ATC | AGC | CCT | GAT | TTG | GTC | AGG | GAG | 255 |
| TTT | CCA | GAT | GTT | TTG | GAA | TGT | ACC | ATG | TCC | CAT | GCA | GTG | 294 |
| GAA | AAG | ATA | AAC | CCT | GAT | GAA | AGA | GAA | GAA | ATG | AAA | GTT | 333 |
| TCT | GCT | AAA | CTG | TTC | ATT | GTA | GGA | TCG | AAT | TCT | TCA | TCA | 372 |
| TCA | ACT | AGA | AAT | GCA | GTT | GAC | ATG | GCA | TGC | TCA | GTC | CTT | 411 |
| GGA | GTT | GCA | CAG | CTG | GAC | TCT | GTC | ATC | ATG | GCT | TCC | CCT | 450 |
| CCA | ATT | GAA | GAT | GGA | GTT | AAT | CTT | TCC | TTG | GAG | CAT | TTG | 489 |
| CAG | CCT | TAC | TGG | GAG | GAA | TTA | GAA | AAC | TTA | GTT | CAG | AGC | 528 |

| | | | | | | | | | | | | | |
|---|---|---|---|---|---|---|---|---|---|---|---|---|---|
|AAG|AAG|ATT|GTT|GCT|ATA|GGC|ACC|TCG|GAT|CTA|GAC|AAA|567|
|ACA|CAG|TTG|GAG|CAG|CTG|TAC|CAG|TGG|GCA|CAG|GTA|AAA|606|
|CCC|AAT|AGT|AAT|CAA|GTT|AAT|CTT|GCC|TCC|TGC|TGT|GTG|645|
|ATG|CCA|CCA|GAT|TTG|ACT|GCA|TTT|GCT|AAA|CAG|TTT|GAC|684|
|ATA|CAG|CTA|CTG|ACT|CAC|AAT|GAC|CCA|AAA|GAA|CTG|CTC|723|
|TCT|GAG|GCA|AGT|TTC|CAG|GAA|GCT|CTT|CAA|GAA|AGC|ATC|762|
|CCT|GAC|ATT|GAA|GCC|CAG|GAG|TGG|GTG|CCA|CTG|TGG|CTG|801|
|CTG|AGG|TAC|TCG|GTC|ATC|GTG|AAA|AGC|AGA|GGA|ATC|ATC|840|
|AAG|TCA|AAA|GGA|TAC|ATT|TTG|CAA|GCC|AAA|AGA|AAG|GGT|879|
|TCT|882| | | | | | | | | | | | |
|TAACTACAGC|TCAAGCTCAC|AACTCAGGGG|CCTTGTATTT|ATCTGGAACA|932| | | | | | | | |
|TAAGATAAAA|ATTCATGATA|AAATTGAGAT|GTGTAAAAAA|AAATCTAGCT|982| | | | | | | | |
|CTCGCCTACA|AAAAGCGTCA|CTGAGGCGTG|AATGTGGTGG|TTTGGCAATG|1032| | | | | | | | |
|TGTTGAGTTT|AAGTACCTCC|CTGGCGTCTG|CAGCAGCGCA|CTCACAGGAA|1082| | | | | | | | |
|GCATTGTATT|CTCTTCATTA|AACTCTTGGT|TTCTAACTGA|AATCGTCTAT|1132| | | | | | | | |
|AAAGAAAAAT|ACTTGCAATA|TATTTCCTTT|ATTTTTATGA|GTAATAGAAA|1182| | | | | | | | |
|TCAAGAAAAT|TTGTTTTAAG|ATATATTTTG|GCTTAGGCAT|CAGGGTGATG|1232| | | | | | | | |
|TATATACATA|TTTTTTATTT|CTAAAATTCA|GTAACTGCTT|CTTACTCTAT|1282| | | | | | | | |
|ACTTCTATAA|CTAAGCAATT|ACATTACAGT|TGTTAAGACA|TACTGGAAGA|1332| | | | | | | | |
|GATTTTTTTC|CTGTCGTTTG|ACAAAATAAT|CTATCTCAGA|GTCGGAATTC|1382| | | | | | | | |

The sequence according to the present invention contains 1382 nucleotides and a open reading frame, indicated by triplet codons, of 822 nucleotides coding for 274 amino acid residues. The cDNA also has a 5'-nontranslational region of 60 nucleotides and a 3'-nontranslational region of 500 nucleotides. The first ATG (position 61) is presumed to be the initiation codon because (a) the nucleotide sequence surrounding this codon (... GCCATGG ...) agrees with the consensus sequence for eukaryotic initiation sites described by Kozak [see Nucleic Acid Research 12:857 (1984)] and (b) expression of the cDNA using this ATG as initiation codon produces a protein that co-migrates with the light subunit of isolated holoenzyme. The open reading frame sequence ends with a termination codon (TAA) at position 883, followed by 10 other termination codons. The predicted protein sequence, which contains the two independently determined peptide sequence (total 41 residues; 139–156 and 219–241), was found to be unique when compare with the protein sequence given in the Genbank# data base. The expressed open reading frame for the light subunit of γ-glutamylcysteine synthetase according to the present invention provides for the following peptide in which the two independently determined peptide sequence above are underlined is:

| | | | | | | | | | | | | | | |
|---|---|---|---|---|---|---|---|---|---|---|---|---|---|---|
|Met|Gly|Thr|Asp|Ser 5|Arg|Ala|Ala|Gly|Ala 10|Leu|Leu|Ala|Arg|Ala 15|
|Ser|Thr|Leu|His|Leu 20|Gln|Thr|Gly|Asn|Leu 25|Leu|Asn|Trp|Gly|Arg 30|
|Leu|Arg|Lys|Lys|Cys 35|Pro|Ser|Thr|His|Ser 40|Glu|Glu|Leu|Arg|Asp 45|
|Cys|Ile|Gln|Lys|Thr 50|Leu|Asn|Glu|Trp|Ser 55|SEr|Gln|Ile|Ser|Pro 60|
|Asp|Leu|Val|Arg|Glu 65|Phe|Pro|Asp|Val|Leu 70|Glu|Cys|Thr|Met|Ser 75|
|His|Ala|Val|Glu|Lys 80|Ile|Asn|Pro|Asp|Glu 85|Arg|Glu|Glu|Met|Lys 90|
|Val|Ser|Ala|Lys|Leu 95|Phe|Ile|Val|Gly|Ser 100|Asn|Ser|Ser|Ser|Ser 105|
|Thr|Arg|Asn|Ala|Val 110|Asp|Met|Ala|Cys|Ser 115|Val|Leu|Gly|Val|Ala 120|
|Gln|Leu|Asp|Ser|Val 125|Ile|Met|Ala|Ser|Pro 130|Pro|Ile|Glu|Asp|Gly 135|
|Val|Asn|Leu|Ser|Leu 140|Glu|His|Leu|Gln|Pro 145|Tyr|Trp|Glu|Glu|leu 150|
|Glu|Asn|Leu|Val|Gln 155|Ser|Lys|Lys|Ile|Val 160|Ala|Ile|Gly|Thr|Ser 165|
|Asp|Leu|Asp|Lys|Thr 170|Gln|Leu|Glu|Gln|Leu 175|Tyr|Gln|Trp|Ala|Gln 180|
|Val|Lys|Pro|Asn|Ser 185|Asn|Gln|Val|Asn|Leu 190|Ala|Ser|Cys|Cys|Val 195|
|Met|Pro|Pro|Asp|Leu 200|Thr|Ala|Phe|Ala|Lys 205|Gln|Phe|Asp|Ile|Gln 210|
|Leu|Leu|Thr|His|Asn 215|Asp|Pro|Lys|Glu|Leu 220|Leu|Ser|Glu|Ala|Ser 225|
|Phe|Gln|Glu|Ala|Leu 230|Gln|Glu|Ser|Ile|Pro 235|Asp|Ile|Glu|Ala|Gln 240|
|Glu|Trp|Val|Pro|Leu|Trp|Leu|Leu|Arg|Tyr|Ser|Val|Ile|Val|Lys|

|     |     |     |     | 245 |     |     |     |     | 250 |     |     |     |     | 255 |
| --- | --- | --- | --- | --- | --- | --- | --- | --- | --- | --- | --- | --- | --- | --- |
| Ser | Arg | Gly | Ile | Ile | Lys | Ser | Lys | Gly | Tyr | Ile | Leu | Gln | Ala | Lys |
|     |     |     |     | 260 |     |     |     |     | 265 |     |     |     |     | 270 |
| Arg | Lys | Gly | Ser |     |     |     |     |     |     |     |     |     |     |     |

The amino acid composition of the light subunit of rat kidney γ-glutamylcysteine synthetase is as follows:

| Amino acid | Isolated subunit | Deduced from the cDNA sequence |
| --- | --- | --- |
| Axs | 43 | 26 |
| Glx | 47 | 37 |
| Cys* | 7 | 6 |
| Ser | 26 | 29 |
| Gly | 22 | 11 |
| His | 8 | 5 |
| Arg | 12 | 11 |
| Thr | 10 | 11 |
| Ala | 19 | 20 |
| Pro | 19 | 13 |
| Tyr | 5 | 4 |
| Val | 17 | 18 |
| Met | 7 | 6 |
| Ile | 12 | 15 |
| Leu | 35 | 33 |
| Phe | 7 | 5 |
| Lys | 18 | 17 |
| Trp |  | 6 |

*determined as carboxymethylated cysteine

EXAMPLE VIII

The construction of a light subunit expression plasmid was conducted according to the following:

The light subunit cDNA in plasmid pBluescript KS was digested with NcoI; the DNA was filled-in with four dNTPs using T4 DNA polymerase and subsequently treated with BamHI [see Sambrook, supra]. The resulting DNA fragment (1 kb) was ligated [see Sambrook, supra] into expression vector pT7—7 which had previously been digested with NdeI (filled-in) and BamHI. The resulting plasmid (pRGCSL) (see FIG. 1) contains the light subunit cDNA immediately downstream of a T7 promoter.

This plasmid is on deposit at the Cornell University Medical College, 1300 York Avenue, New York, N.Y., and will be made available to anyone requesting the plasmid from the inventors hereof in accordance with the Budapest Treaty.

EXAMPLE IX

Figure 2:
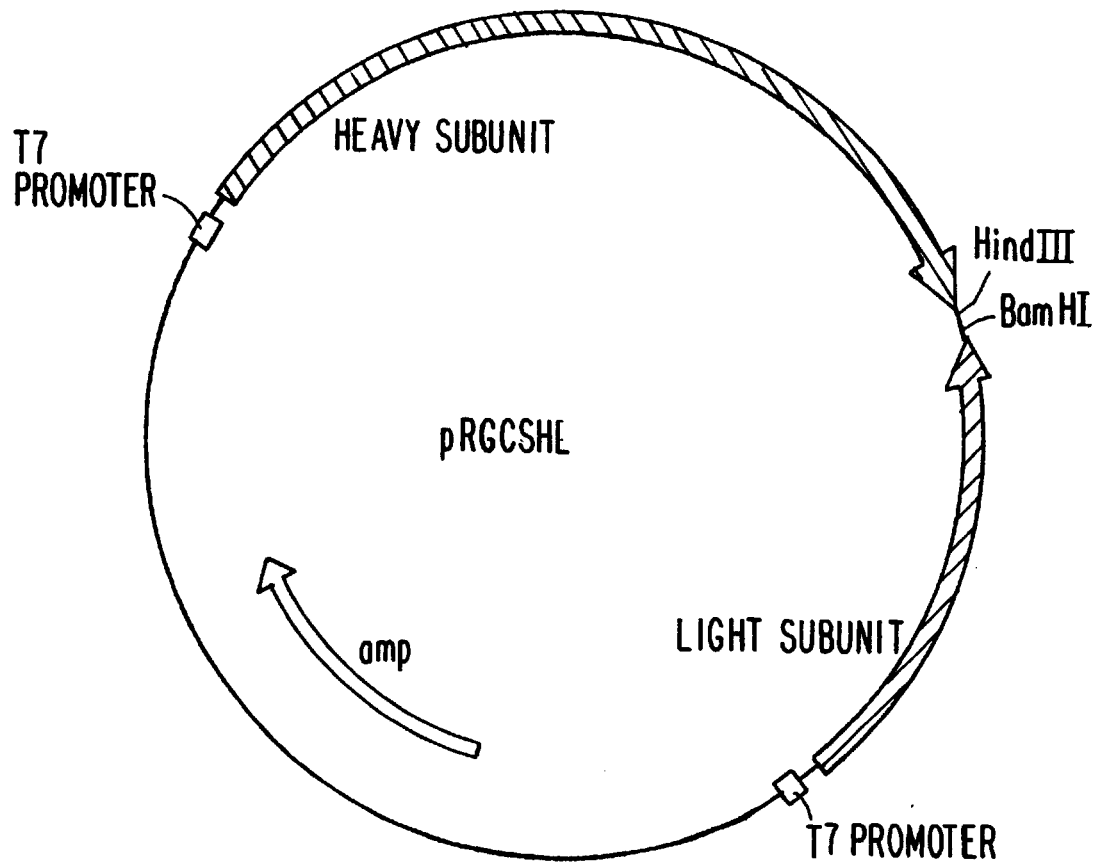
FIG. 2 represents the co-expression plasmid, pRGCSHL, according to the present invention.
Figure 3:
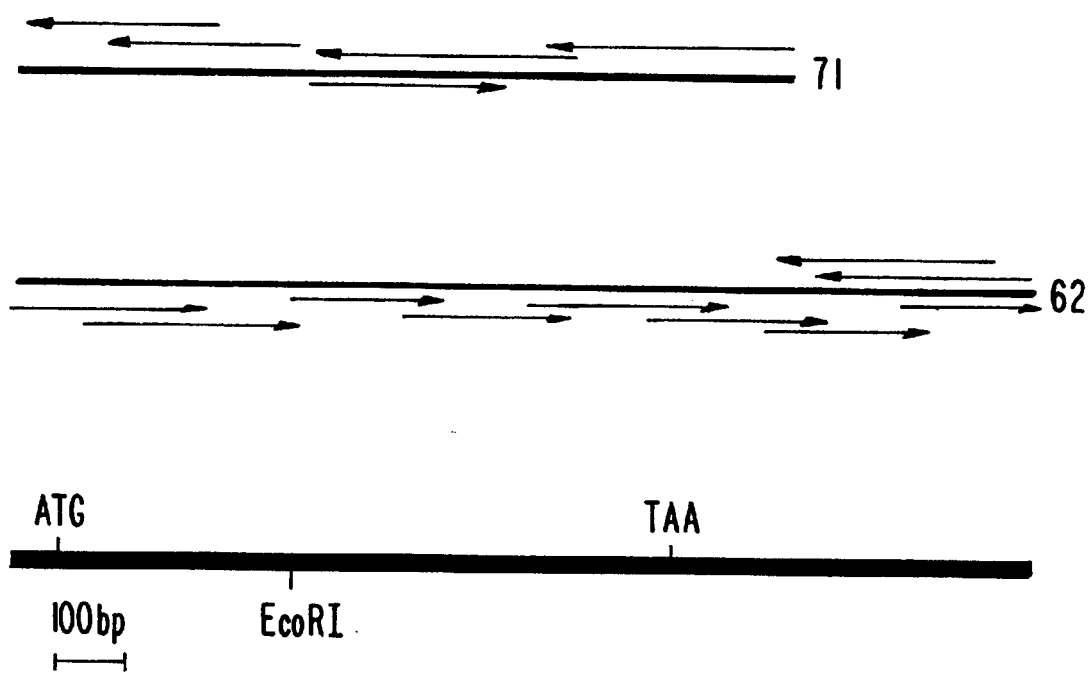
FIG. 3 represents the sequencing strategy for Clones 71 and 62 according to the present invention.

A co-expression plasmid in accordance with the present invention was constructed as follows:

The expression plasmid for the heavy subunit pRGCSH [see J. Biol. Chem (1993)] was digested with BstBl. The DNA was filled-in [see Sambrook, supra] using T4 DNA polymerase followed by digestion with Hind 111. The resulting 2-kb DNA fragment that contains a T7 promoter and the heavy subunit cDNA was ligated to plasmid pRGCSL (see FIG. 1) which had been previously treated with ClaI (filled-in) and HindIII. The plasmid obtained (pRGCSHL) (see FIG. 2) contains two T7 promoters in opposite directions immediately followed by the heavy and the light subunit respectively.

EXAMPLE X

Purification of recombinant holoenzyme was conducted as follows:

Co-expression plasmid pRGCSHL (1 ng) was transformed into E coli BL21(DE3). This organism is on deposit at the Cornell University Medical College, 1300 York Avenue, New York, N.Y., and will be made available to anyone requesting the plasmid-containing organism from the inventors hereof in accordance with the Budapest Treaty. The recombinant holoenzyme was expressed according to known methods as described in the literature [see J. Biol. Chem (1993)]. The enzyme was purified in the manner similar to that used in purification of the recombinant heavy subunit using recognized techniques [see Sambrook, supra]. The enzyme isolated from the ATP-agarose column was further purified on a ProteinPak™ 300 (Waters) HPLC gel filtration column previously equilibrated with imidazole buffer (10 mM; pH 7.4) containing 1 mM EDTA.

The purified recombinant holoenzyme exhibited a specific activity of 1,250 when assayed in a assay solution that contains 10 mM glutamate as depicted in the following table. This specific activity is similar to that of the holoenzyme isolated from rat kidney but is much higher.

Isolation Of Recombinant γ-glutamylcysteine synthetase holoenzyme

| Step: | Volume (ml) | Protein (mg) | Activity (units) | Specific Activity (units/mg) |
| --- | --- | --- | --- | --- |
| 1 - Extract | 61 | 520 | 6230 | 12 |
| 2 - DE52 | 120 | 95 | 5150 | 54 |
| 3 - ATP-agarose | 11.5 | 6.4 | 4750 | 742 |
| 4 - Protein Pak 300 | 4.6 | 3.4 | 4230 | 250 |

The following table presents the $K_m$ values for the holoenzyme and heavy subunit of the GSH enzyme. In this table, the Km value is a reflection of the affinity of the substrate for the enzyme; a high value meaning a low affinity, and a low value means a high affinity.

Apparent $K_m$ values (mM) for γ-glutamylcysteine synthetase

| Enzyme preparation | glutamate | a-aminobutyrate | cysteine |
| --- | --- | --- | --- |
| Isolated holoenzyme | 1.4 | 1.2 | 0.2 |
| Co-expressed recombinant holoenzyme | 1.8 | 1.1 | 0.2 |
| Recombinant holoenzyme (mixed) | 2.8 | 1.2 | 0.2 |
| Recombinant heavy subunit | 18.2 | 0.8 | 0.2 |

Thus, this table illustrates that the two types of recombinant enzyme (one made by co-expressing cDNA for light and cDNA for heavy subunits—and the other by simply mixing the separately expressed subunits) have affinity for glutamate, cysteine (and alpha-aminobutyrate) that is about the same as the isolated holoenzyme. However, the recombinant heavy enzyme has a value of 18.2 mM for glutamate indicating that this enzyme has about a 10-fold lower affinity for glutamate. This is, in fact, a key point of the present invention: it is shown that the heavy subunit alone (without the light) has too low an affinity for one of the substrates (glutamate) to be useful physiologically. Note also that the value for glutamate for the recombinant holoenzyme prepared by mixing the separately expressed light and heavy subunit is 2.8 mM, suggesting that mixing the subunits is not quite as efficient as co-expressing the subunits.

With present technology, it is possible to synthesize either the nucleotide or peptide sequences according to the present invention using automated procedures. For example, the nucleotide sequence may be directly synthesized on an automated DNA synthesizer such as the Applied Biosystems Model 380A. At the time of synthesis, a large number of base, ribose and phosphate modifications can also be incorporated by substitution of the appropriate reagents for normal phosphoramidite chemistry.

Small oligonucleotides are spontaneously taken up from the surrounding medium by some cells, and this technique may be used to introduce the oligonucleotide according to the present invention into the appropriate cells to increase GSH levels within animal tissues. In addition, it is also within the present day purview of those skilled in the art to develop antisense sequences to the oligonucleotides according to the present invention and to introduce such antisense sequences into appropriate cells to inhibit GSH levels within animal tissues. Such uptake of both sense and antisense oligonucleotides may be facilitate by modification of the nucleic acid, as a derivatization with a hydrophobic moiety, substitution of methylphosphonates, phosphorothioates or dithiotes for normally occurring phosphates. Liposome fusion provides another mode of delivering nucleic acid-based reagents to cells. Such techniques for manufacturing and delivery of oligonucleotides and peptides are well know in the art.

Thus, following the detailed description of the present invention and the examples contained therein, it can be deduced that the presented 274 amino acid sequence leads to a molecular weight (30,548) which is higher than that previously estimated (27,700) for the light subunit by SDS gel electrophoresis, and the calculated amino acid composition is in fair agreement with that determined by amino acid analysis of the isolated light subunit.

Potential useful applications of the present invention include the possibility of increasing the amount of enzyme present in an animal by gene transfer (so-called "gene therapy").

A model for this type of gene transfer and for its potential usefulness has been found in connection with studies on a strain of $E.$ $coli$ whose radioresistance was enhanced by enrichment of its content of the enzyme required for glutathione synthesis by recombinant DNA techniques [see Proc. Natl. Acad. Sci. U.S. 86:1461 (1989)]. Gene transfer of the gene of the present invention would also be expected to give a similar result, and it would also be expected that the biochemical reactions associated with glutathione would also be enhanced by such a genetic transfer of this gene into an animal host. Of course, in most instances this gene would be transferred into the animal host along with promoters, inducers, and the like (which are well known and recognized techniques in the field of genetic engineering) to allow the cell to initiate and continue production of the genetic product protein. However, such potential applications are still not ready for commercialization, because of clinical testing and federal approvals required to routinely treat animals, including man, to increase their body's production of glutathione. Another potential application within the purview of the present application as described above is to introduce antisense oligonucleotide sequences to a cell as a means to inhibit GSH production by the cell. An earlier commercial use of the present invention is the potential of using the probes described above to assay and measure the concentration of mRNA for the enzyme in clinical specimens obtained from animal sources. The technology is in place to develop such a test around the present invention.

A sequence listing of all nucleotide and peptide sequences disclosed herein follows:

SEQUENCE LISTING ( 1 ) GENERAL INFORMATION:

( i i i ) NUMBER OF SEQUENCES: 10

( 2 ) INFORMATION FOR SEQ ID NO: 1:

( i ) SEQUENCE CHARACTERISTICS:
        ( A ) LENGTH: 23 amino acids
        ( B ) TYPE: Amino Acid
        ( D ) TOPOLOGY: linear ( i i ) MOLECULE TYPE: peptide ( x i ) SEQUENCE DESCRIPTION: SEQ ID NO: 1:

```
Glu  Leu  Leu  Ser  Glu  Ala  Ser  Phe  Gln  Glu  Ala  Leu  Gln  Glu  Ser
                    5                        10                       15
Ile  Pro  Asp  Ile  Glu  Ala  Gln  Glu
                    20
```

( 2 ) INFORMATION FOR SEQ ID NO: 2:

( i ) SEQUENCE CHARACTERISTICS:
        ( A ) LENGTH: 18 amino acids
        ( B ) TYPE: Amino Acid
        ( D ) TOPOLOGY: linear (ii) MOLECULE TYPE: peptide (ix) FEATURE:
    (D) OTHER INFORMATION: position 9 is a undetermined sequence (xi) SEQUENCE DESCRIPTION: SEQ ID NO: 2:

Ser Leu Glu His Leu Gln Pro Tyr Xaa Glu Glu Leu Glu Asn Leu
                  5                   10                  15
Val Gln Ser (2) INFORMATION FOR SEQ ID NO: 3:

(i) SEQUENCE CHARACTERISTICS:
        (A) LENGTH: 7 amino acids
        (B) TYPE: Amino Acid
        (D) TOPOLOGY: linear (ii) MOLECULE TYPE: peptide (xi) SEQUENCE DESCRIPTION: SEQ ID NO: 3:

Phe Gln Glu Ala Leu Gln Glu
              5

(2) INFORMATION FOR SEQ ID NO: 4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: mRNA (xi) SEQUENCE DESCRIPTION: SEQ ID NO: 4:

UUU CAA GAA GCU CUU CAA GAA                                         21

(2) INFORMATION FOR SEQ ID NO: 5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: the designation "N" at
            positions 12 and 15 represent deoxyinosine (xi) SEQUENCE DESCRIPTION: SEQ ID NO: 5:

TTT CAA GAA GCN CTN CAA GA                                          20

(2) INFORMATION FOR SEQ ID NO: 6:

(i) SEQUENCE CHARACTERISTICS:
        (A) LENGTH: 1382 base pairs
        (B) TYPE: Nucleic Acid
        (C) STRANDEDNESS: single
        (D) TOPOLOGY: linear (ii) MOLECULE TYPE: cDNA (xi) SEQUENCE DESCRIPTION: SEQ ID NO: 6:

GAATTCCGGC CTTCCCTCCG TGGCTCCGGC GCTGCCCGGT CCCCTCGGGC               50

GGCAGCTGCC                                                          60

ATG GGC ACC GAC AGC CGC GCG GCC GGA GCA CTT CTG GCG                 99

```
CGG GCC AGC ACC CTG CAC CTG CAG ACC GGG AAC CTG CTC        138
AAC TGG GGC CGC CTG CGG AAA AAG TGT CCG TCC ACG CAC        177
AGC GAG GAG CTT CGA GAC TGT ATC CAA AAG ACC TTG AAT        216
GAA TGG AGC TCC CAA ATC AGC CCT GAT TTG GTC AGG GAG        255
TTT CCA GAT GTT TTG GAA TGT ACC ATG TCC CAT GCA GTG        294
GAA AAG ATA AAC CCT GAT GAA AGA GAA GAA ATG AAA GTT        333
TCT GCT AAA CTG TTC ATT GTA GGA TCG AAT TCT TCA TCA        372
TCA ACT AGA AAT GCA GTT GAC ATG GCA TGC TCA GTC CTT        411
GGA GTT GCA CAG CTG GAC TCT GTC ATC ATG GCT TCC CCT        450
CCA ATT GAA GAT GGA GTT AAT CTT TCC TTG GAG CAT TTG        489
CAG CCT TAC TGG GAG GAA TTA GAA AAC TTA GTT CAG AGC        528
AAG AAG ATT GTT GCT ATA GGC ACC TCG GAT CTA GAC AAA        567
ACA CAG TTG GAG CAG CTG TAC CAG TGG GCA CAG GTA AAA        606
CCC AAT AGT AAT CAA GTT AAT CTT GCC TCC TGC TGT GTG        645
ATG CCA CCA GAT TTG ACT GCA TTT GCT AAA CAG TTT GAC        684
ATA CAG CTA CTG ACT CAC AAT GAC CCA AAA GAA CTG CTC        723
TCT GAG GCA AGT TTC CAG GAA GCT CTT CAA GAA AGC ATC        762
CCT GAC ATT GAA GCC CAG GAG TGG GTG CCA CTG TGG CTG        801
CTG AGG TAC TCG GTC ATC GTG AAA AGC AGA GGA ATC ATC        840
AAG TCA AAA GGA TAC ATT TTG CAA GCC AAA AGA AAG GGT        879
TCT                                                        882

TAACTACAGC TCAAGCTCAC AACTCAGGGG CCTTGTATTT ATCTGGAACA      932
TAAGATAAAA ATTCATGATA AAATTGAGAT GTGTAAAAAA AAATCTAGCT      982
CTCGCCTACA AAAAGCGTCA CTGAGGCGTG AATGTGGTGG TTTGGCAATG     1032
TGTTGAGTTT AAGTACCTCC CTGGCGTCTG CAGCAGCGCA CTCACAGGAA     1082
GCATTGTATT CTCTTCATTA AACTCTTGGT TTCTAACTGA AATCGTCTAT     1132
AAAGAAAAAT ACTTGCAATA TATTTCCTTT ATTTTTATGA GTAATAGAAA     1182
TCAAGAAAAT TTGTTTTAAG ATATATTTTG GCTTAGGCAT CAGGGTGATG     1232
TATATACATA TTTTTTATTT CTAAAATTCA GTAACTGCTT CTTACTCTAT     1282
ACTTCTATAA CTAAGCAATT ACATTACAGT TGTTAAGACA TACTGGAAGA     1332
GATTTTTTTC CTGTCGTTTG ACAAAATAAT CTATCTCAGA GTCGGAATTC     1382
```

( 2 ) INFORMATION FOR SEQ ID NO: 7:

( i ) SEQUENCE CHARACTERISTICS:
        ( A ) LENGTH: 274 amino acids
        ( B ) TYPE: Amino Acid
        ( D ) TOPOLOGY: linear ( i i ) MOLECULE TYPE: peptide ( x i ) SEQUENCE DESCRIPTION: SEQ ID NO: 7:

```
Met  Gly  Thr  Asp  Ser  Arg  Ala  Ala  Gly  Ala  Leu  Leu  Ala  Arg  Ala
               5                   10                       15

Ser  Thr  Leu  His  Leu  Gln  Thr  Gly  Asn  Leu  Leu  Asn  Trp  Gly  Arg
20                   25                       30
```

| | | | | | | | | | | | | | | |
|---|---|---|---|---|---|---|---|---|---|---|---|---|---|---|
| Leu | Arg | Lys | Lys | Cys | Pro | Ser | Thr | His | Ser | Glu | Glu | Leu | Arg | Asp |
| 35 | | | | 40 | | | | | 45 | | | | | |
| Cys | Ile | Gln | Lys | Thr | Leu | Asn | Glu | Trp | Ser | Ser | Gln | Ile | Ser | Pro |
| | | | | 50 | | | | 55 | | | | | | 60 |
| Asp | Leu | Val | Arg | Glu | Phe | Pro | Asp | Val | Leu | Glu | Cys | Thr | Met | Ser |
| | | | | 65 | | | | | 70 | | | | | 75 |
| His | Ala | Val | Glu | Lys | Ile | Asn | Pro | Asp | Glu | Arg | Glu | Glu | Met | Lys |
| | | | | 80 | | | | | 85 | | | | | 90 |
| Val | Ser | Ala | Lys | Leu | Phe | Ile | Val | Gly | Ser | Asn | Ser | Ser | Ser | Ser |
| | | | | 95 | | | | | 100 | | | | | 105 |
| Thr | Arg | Asn | Ala | Val | Asp | Met | Ala | Cys | Ser | Val | Leu | Gly | Val | Ala |
| | | | | 110 | | | | | 115 | | | | | 120 |
| Gln | Leu | Asp | Ser | Val | Ile | Met | Ala | Ser | Pro | Pro | Ile | Glu | Asp | Gly |
| | | | | 125 | | | | | 130 | | | | | 135 |
| Val | Asn | Leu | Ser | Leu | Glu | His | Leu | Gln | Pro | Tyr | Trp | Glu | Glu | Leu |
| | | | | 140 | | | | | 145 | | | | | 150 |
| Glu | Asn | Leu | Val | Gln | Ser | Lys | Lys | Ile | Val | Ala | Ile | Gly | Thr | Ser |
| | | | | 155 | | | | | 160 | | | | | 165 |
| Asp | Leu | Asp | Lys | Thr | Gln | Leu | Glu | Gln | Leu | Tyr | Gln | Trp | Ala | Gln |
| | | | | 170 | | | | | 175 | | | | | 180 |
| Val | Lys | Pro | Asn | Ser | Asn | Gln | Val | Asn | Leu | Ala | Ser | Cys | Cys | Val |
| | | | | 185 | | | | | 190 | | | | | 195 |
| Met | Pro | Pro | Asp | Leu | Thr | Ala | Phe | Ala | Lys | Gln | Phe | Asp | Ile | Gln |
| | | | | 200 | | | | | 205 | | | | | 210 |
| Leu | Leu | Thr | His | Asn | Asp | Pro | Lys | Glu | Leu | Leu | Ser | Glu | Ala | Ser |
| | | | | 215 | | | | | 220 | | | | | 225 |
| Phe | Gln | Glu | Ala | Leu | Gln | Glu | Ser | Ile | Pro | Asp | Ile | Glu | Ala | Gln |
| | | | | 230 | | | | | 235 | | | | | 240 |
| Glu | Trp | Val | Pro | Leu | Trp | Leu | Leu | Arg | Tyr | Ser | Val | Ile | Val | Lys |
| | | | | 245 | | | | | 250 | | | | | 255 |
| Ser | Arg | Gly | Ile | Ile | Lys | Ser | Lys | Gly | Tyr | Ile | Leu | Gln | Ala | Lys |
| | | | | 260 | | | | | 265 | | | | | 270 |
| Arg | Lys | Gly | Ser | | | | | | | | | | | |

( 2 ) INFORMATION FOR SEQ ID NO: 8:

( i ) SEQUENCE CHARACTERISTICS:
    ( A ) LENGTH: 20 base pairs
    ( B ) TYPE: Nucleic Acid
    ( C ) STRANDEDNESS: single
    ( D ) TOPOLOGY: linear ( i i ) MOLECULE TYPE: DNA ( x i ) SEQUENCE DESCRIPTION: SEQ ID NO: 8:

TTC CAG GAA GCT CTT CAA GA  20

( 2 ) INFORMATION FOR SEQ ID NO: 9:

( i ) SEQUENCE CHARACTERISTICS:
    ( A ) LENGTH: 1914 base pairs
    ( B ) TYPE: Nucleic Acid
    ( C ) STRANDEDNESS: single
    ( D ) TOPOLOGY: linear ( i i ) MOLECULE TYPE: DNA ( x i ) SEQUENCE DESCRIPTION: SEQ ID NO: 9:

ATG GGG CTG CTG TCC CAA GGC TCG CCA CTG AGC TGG GAA  39

```
GAG ACC CAG CGC CAC GCC GAC CAC GTG CGG AGA CAC GGC          78
ATC CTC CAG TTC CTG CAC ATC TAC CAC GCA GTC AAG GAC         117
CGG CAC AAG GAC GTG CTC AAG TGG GGT GAC GAG GTG GAG         156
TAC ATG TTG GTG TCC TTT GAT CAT GAA AAT AGG AAA GTC         195
CAG TTG TTA CTG AAT GGC GGC GAT GTT CTT GAA ACT CTG         234
CAA GAG AAG GGG GAG AGG ACA AAC CCC AAC CAC CCA ACC         273
CTC TGG AGA CCA GAG TAT GGG AGT TAC ATG ATT GAA GGG         312
ACA CCT GGC CAG CCG TAC GGA GGA ACG ATG TCC GAG TTC         351
AAC ACA GTG GAG GAC AAC ATG AGG AAA CGC CGG AAG GAG         390
GCT ACT TCT GTA TTA GGA GAA CAT CAG GCT CTT TCG ACG         429
ATA ACT TCA TTT CCC AGG CTA GGC TGC CCT GGA TTC ACA         468
CTG CCA GAG CAC AGA CCC AAC CCA GAG GAA GGA GGT GCA         507
TCT AAG TCC CTC TTC TTT CCA GAC GAA GCC ATA AAC AAG         546
CAC CCC CGC TTT GGT ACT CTA ACA AGA AAC ATC CGG CAT         585
CGG AGA GGA GAA AAG GTT GTC ATC AAT GTG CCA ATA TTC         624
AAG GAC AAG AAC ACA CCA TCT CCG TTT GTA GAA ACA TTT         663
CCT GAG GAT GAG GAG GCA TCA AAG GCC TCT AAG CCA GAC         702
CAC ATC TAC ATG GAT GCC ATG GGA TTT GGG ATG GGC AAC         741
TGC TGT CTT CAG GTG ACA TTC CAA GCC TGC AGT ATA TCT         780
GAG GCA AGA TAC CTT TAT GAC CAG TTG GCC ACT ATC TGC         819
CCA ATT GTT ATG GCT TTG AGT GCT GCA TCG CCA TTT TAC         858
CGA GGC TAC GTG TCA GAC ATT GAT TGT CGC TCG GGA GTG         897
ATT TCT GCA TCT GTA GAT GAT AGA ACA CGG GAG GAG AGA         936
GGA CTG GAG CCC CTG AAG AAC AAT CGC TTT AAA ATC AGT         975
AAG TCT CGG TAT GAC TCA ATA GAT AGC TAC CTG TCC AAG        1014
TGT GGA GAG AAG TAC AAT GAC ATC GAC CTG ACC ATC GAC        1053
ACG GAG ATC TAC GAG CAG CTC TAA GAG GAA GGC ATC GAT        1092
CAC CTT CTG GCA CAG CAG GTT GCT CAT CTC TTT ATT AGA        1131
GAC CCA CTG ACC CTT TTT GAA GAG AAA ATT CAT CTG GAT        1170
GAT GCC AAC GAG TCT GAC CAT TTT GAG AAT ATT CAG TCC        1209
ACA AAC TGG CAG ACA ATG AGG TTT AAG CCT CCT CCT CCA        1248
AAC TCA GAT ATT GGA TGG AGA GTA GAG TTC CGA CCA ATG        1287
GAG GTA CAG TTG ACA GAC TTT GAG AAC TCT GCC TAT GTG        1326
GTA TTT GTG GTA CTG CTG ACC AGG GTG ATC CTC TCA TAC        1365
AAA CTA GAC TTC CTC ATT CCA CTG TCC AAG GTT GAC GAG        1404
AAC ATG AAA GTG GCA CAG GAG CGA GAT GCC GTC TTA CAG        1443
GGG ATG TTT TAT TTC AGG AAA GAC ATT TGC AAA GGT GGC        1482
AAC GCC GTG GTG GAT GGG TGT AGC AAG GCC CAG ACC AGC        1521
TCC GAG CCA TCT GCA GAG GAG TAC ACG CTC ATG AGC ATA        1560
GAC ACC ATC ATC AAT GGG AAG GAA GGC GTG TTT CCT GGA        1599
```

-continued

| | | | | | | | | | | | | | |
|---|---|---|---|---|---|---|---|---|---|---|---|---|---|
| CTC | ATC | CCC | ATT | CTG | AAC | TCC | TAC | CTT | GAA | AAC | ATG | GAA | 1638 |
| GTC | GAC | GTG | GAC | ACC | CGA | TGC | AGT | ATT | CTG | AAC | TAC | CTG | 1677 |
| AAG | CTA | ATT | AAG | AAG | AGA | GCA | TCT | GGA | GAA | CTA | ATG | ACT | 1716 |
| GTT | GCC | AGG | TGG | ATG | AGA | GAG | TTT | ATT | GCA | AAC | CAT | CCT | 1755 |
| GAC | TAC | AAG | CAA | GAC | AGT | GTA | ATA | ACT | GAT | GAG | ATC | AAC | 1794 |
| TAT | AGC | CTC | ATT | TTG | AAA | TGC | AAT | CAA | ATT | GCA | AAT | GAA | 1833 |
| TTG | TGT | GAA | TGT | CCA | GAG | TTA | CTT | GGA | TCA | GGC | TTT | AGA | 1872 |
| AAA | GCG | AAG | TAC | AGT | GGA | GGT | AAA | AGC | GAC | CCT | TCA | GAC | 1911 |
| TAG | | | | | | | | | | | | | 1914 |

( 2 ) INFORMATION FOR SEQ ID NO: 10:

( i ) SEQUENCE CHARACTERISTICS:
        ( A ) LENGTH: 637 amino acids
        ( B ) TYPE: Amino Acid
        ( D ) TOPOLOGY: linear ( i i ) MOLECULE TYPE: peptide ( x i ) SEQUENCE DESCRIPTION: SEQ ID NO: 10:

| | | | | | | | | | | | | | | |
|---|---|---|---|---|---|---|---|---|---|---|---|---|---|---|
| Met | Gly | Leu | Leu | Ser | Gln | Gly | Ser | Pro | Leu | Ser | Trp | Glu | Glu | Thr |
| | | | | 5 | | | | | 10 | | | | | 15 |
| Gln | Arg | His | Ala | Asp | His | Val | Arg | Arg | His | Gly | Ile | Leu | Gln | Phe |
| | | | | 20 | | | | | 25 | | | | | 30 |
| Leu | His | Ile | Tyr | His | Ala | Val | Lys | Asp | Arg | His | Lys | Asp | Val | Leu |
| | | | | 35 | | | | | 40 | | | | | 45 |
| Lys | Trp | Gly | Asp | Glu | Val | Glu | Tyr | Met | Leu | Val | Ser | Phe | Asp | His |
| | | | | 50 | | | | | 55 | | | | | 60 |
| Glu | Asn | Arg | Lys | Val | Gln | Leu | Leu | Leu | Asn | Gly | Gly | Asp | Val | Leu |
| | | | | 65 | | | | | 70 | | | | | 75 |
| Glu | Thr | Leu | Gln | Glu | Lys | Gly | Glu | Arg | Thr | Asn | Pro | Asn | His | Pro |
| | | | | 80 | | | | | 85 | | | | | 90 |
| Thr | Leu | Trp | Arg | Pro | Glu | Tyr | Gly | Ser | Tyr | Met | Ile | Glu | Gly | Thr |
| | | | | 95 | | | | | 100 | | | | | 105 |
| Pro | Gly | Gln | Pro | Tyr | Gly | Gly | Thr | Met | Ser | Glu | Phe | Asn | Thr | Val |
| | | | | 110 | | | | | 115 | | | | | 120 |
| Glu | Asp | Asn | Met | Arg | Lys | Arg | Arg | Lys | Glu | Ala | Thr | Ser | Val | Leu |
| | | | | 125 | | | | | 130 | | | | | 135 |
| Gly | Glu | His | Gln | Ala | Leu | Cys | Thr | Ile | Thr | Ser | Phe | Pro | Arg | Leu |
| | | | | 140 | | | | | 145 | | | | | 150 |
| Gly | Cys | Pro | Gly | Phe | Thr | Leu | Pro | Glu | His | Arg | Pro | Asn | Pro | Glu |
| | | | | 155 | | | | | 160 | | | | | 165 |
| Glu | Gly | Gly | Ala | Ser | Lys | Ser | Leu | Phe | Phe | Pro | Asp | Glu | Ala | Ile |
| | | | | 170 | | | | | 175 | | | | | 180 |
| Asn | Lys | His | Pro | Arg | Phe | Gly | Thr | Leu | Thr | Arg | Asn | Ile | Arg | His |
| | | | | 185 | | | | | 190 | | | | | 195 |
| Arg | Arg | Gly | Glu | Lys | Val | Val | Ile | Asn | Val | Pro | Ile | Phe | Lys | Asp |
| | | | | 200 | | | | | 205 | | | | | 210 |
| Lys | Asn | Thr | Pro | Ser | Pro | Phe | Val | Glu | Thr | Phe | Pro | Glu | Asp | Glu |
| | | | | 215 | | | | | 220 | | | | | 225 |
| Glu | Ala | Ser | Lys | Ala | Ser | Lys | Pro | Asp | His | Ile | Tyr | Met | Asp | Ala |
| | | | | 230 | | | | | 235 | | | | | 240 |
| Met | Gly | Phe | Gly | Met | Gly | Asn | Cys | Cys | Leu | Gln | Val | Thr | Phe | Gln |

-continued

|     |     |     |     | 245 |     |     |     |     | 250 |     |     |     |     | 255 |
|-----|-----|-----|-----|-----|-----|-----|-----|-----|-----|-----|-----|-----|-----|-----|
| Ala | Cys | Ser | Ile | Ser | Glu | Ala | Arg | Tyr | Leu | Tyr | Asp | Gln | Leu | Ala |
|     |     |     |     | 260 |     |     |     |     | 265 |     |     |     |     | 270 |
| Thr | Ile | Cys | Pro | Ile | Val | Met | Ala | Leu | Ser | Ala | Ala | Ser | Pro | Phe |
|     |     |     |     | 275 |     |     |     |     | 280 |     |     |     |     | 285 |
| Tyr | Arg | Gly | Tyr | Val | Ser | Asp | Ile | Asp | Cys | Arg | Trp | Gly | Val | Ile |
|     |     |     |     | 290 |     |     |     |     | 295 |     |     |     |     | 300 |
| Ser | Ala | Ser | Val | Asp | Asp | Arg | Thr | Arg | Glu | Glu | Arg | Gly | Leu | Glu |
|     |     |     |     | 305 |     |     |     |     | 310 |     |     |     |     | 315 |
| Pro | Leu | Lys | Asn | Asn | Arg | Phe | Lys | Ile | Ser | Lys | Ser | Arg | Tyr | Asp |
|     |     |     |     | 320 |     |     |     |     | 325 |     |     |     |     | 330 |
| Ser | Ile | Asp | Ser | Tyr | Leu | Ser | Lys | Cys | Gly | Glu | Lys | Tyr | Asn | Asp |
|     |     |     |     | 335 |     |     |     |     | 340 |     |     |     |     | 345 |
| Ile | Asp | Leu | Thr | Ile | Asp | Thr | Glu | Ile | Tyr | Glu | Gln | Leu | Leu | Glu |
|     |     |     |     | 350 |     |     |     |     | 355 |     |     |     |     | 360 |
| Glu | Gly | Ile | Asp | His | Leu | Leu | Ala | Gln | His | Val | Ala | His | Leu | Phe |
|     |     |     |     | 365 |     |     |     |     | 370 |     |     |     |     | 375 |
| Ile | Arg | Asp | Pro | Leu | Thr | Leu | Phe | Glu | Glu | Lys | Ile | His | Leu | Asp |
|     |     |     |     | 380 |     |     |     |     | 385 |     |     |     |     | 390 |
| Asp | Ala | Asn | Glu | Ser | Asp | His | Phe | Glu | Asn | Ile | Gln | Ser | Thr | Asn |
|     |     |     |     | 395 |     |     |     |     | 400 |     |     |     |     | 405 |
| Trp | Gln | Thr | Met | Arg | Phe | Lys | Pro | Pro | Pro | Asn | Ser | Asp | Ile |     |
|     |     |     |     | 410 |     |     |     |     | 415 |     |     |     | 420 |     |
| Gly | Trp | Arg | Val | Glu | Phe | Arg | Pro | Met | Glu | Val | Gln | Leu | Thr | Asp |
|     |     |     |     | 425 |     |     |     |     | 430 |     |     |     |     | 435 |
| Phe | Glu | Asn | Ser | Ala | Tyr | Val | Val | Phe | Val | Val | Leu | Leu | Thr | Arg |
|     |     |     |     | 440 |     |     |     |     | 445 |     |     |     |     | 450 |
| Val | Ile | Leu | Ser | Tyr | Lys | Leu | Asp | Phe | Leu | Ile | Pro | Leu | Ser | Lys |
|     |     |     |     | 455 |     |     |     |     | 460 |     |     |     |     | 465 |
| Val | Asp | Glu | Asn | Met | Lys | Val | Ala | Gln | Glu | Arg | Asp | Ala | Val | Leu |
|     |     |     |     | 470 |     |     |     |     | 475 |     |     |     |     | 480 |
| Gln | Gly | Met | Phe | Tyr | Phe | Arg | Lys | Asp | Ile | Cys | Lys | Gly | Gly | Asn |
|     |     |     |     | 485 |     |     |     |     | 490 |     |     |     |     | 495 |
| Ala | Val | Val | Asp | Gly | Cys | Ser | Lys | Ala | Gln | Thr | Ser | Ser | Glu | Pro |
|     |     |     |     | 500 |     |     |     |     | 505 |     |     |     |     | 510 |
| Ser | Ala | Glu | Glu | Tyr | Thr | Leu | Met | Ser | Ile | Asp | Thr | Ile | Ile | Asn |
|     |     |     |     | 515 |     |     |     |     | 520 |     |     |     |     | 525 |
| Gly | Lys | Glu | Gly | Val | Phe | Pro | Gly | Leu | Ile | Pro | Ile | Leu | Asn | Ser |
|     |     |     |     | 530 |     |     |     |     | 535 |     |     |     |     | 540 |
| Tyr | Leu | Glu | Asn | Met | Glu | Val | Asp | Val | Asp | Thr | Arg | Cys | Ser | Ile |
|     |     |     |     | 545 |     |     |     |     | 550 |     |     |     |     | 555 |
| Leu | Asn | Tyr | Leu | Lys | Leu | Ile | Lys | Lys | Arg | Ala | Ser | Gly | Glu | Leu |
|     |     |     |     | 560 |     |     |     |     | 565 |     |     |     |     | 570 |
| Met | Thr | Val | Ala | Arg | Trp | Met | Arg | Glu | Phe | Ile | Ala | Asn | His | Pro |
|     |     |     |     | 575 |     |     |     |     | 580 |     |     |     |     | 585 |
| Asp | Tyr | Lys | Gln | Asp | Ser | Val | Ile | Thr | Asp | Glu | Ile | Asn | Tyr | Ser |
|     |     |     |     | 590 |     |     |     |     | 595 |     |     |     |     | 600 |
| Leu | Ile | Leu | Lys | Cys | Asn | Gln | Ile | Ala | Asn | Glu | Leu | Cys | Glu | Cys |
|     |     |     |     | 605 |     |     |     |     | 610 |     |     |     |     | 615 |
| Pro | Glu | Leu | Leu | Gly | Ser | Gly | Phe | Arg | Lys | Ala | Lys | Tyr | Ser | Gly |
|     |     |     |     | 620 |     |     |     |     | 625 |     |     |     |     | 630 |
| Gly | Lys | Ser | Asp | Pro | Ser | Asp |     |     |     |     |     |     |     |     |
|     |     |     |     | 635 |     |     |     |     |     |     |     |     |     |     |

Thus while we have illustrated and described the preferred embodiment of our invention, it is to be understood that this invention is capable of variation and modification, and we therefore do not wish to be limited to the precise terms set forth, but desire to avail ourselves of such changes and alterations which may be made for adapting the invention to various usages and conditions. Accordingly, such changes and alterations are properly intended to be within the full range of equivalents, and therefore within the purview of the following claims.

Having thus described our invention and the manner and a process of making and using it in such full, clear, concise and exact terms so as to enable any person skilled in the art to which it pertains, or with which it is most nearly connected, to make and use the same;

We claim:

1. An isolated nucleic acid molecule encoding mammalian gamma-glutamylcysteine synthetase.

2. The isolated nucleic acid molecule of claim 1 wherein said mammalian gamma-glutamylcysteine synthetase is rat gamma-glutamylcysteine synthetase.

3. The isolated nucleic acid molecule of claim 1 wherein said nucleic acid is deoxyribonucleic acid.

4. The isolated nucleic acid molecule of claim 3 wherein said deoxyribonucleic acid includes the nucleotide sequences as shown in SEQ ID NO:6 and SEQ ID NO:9.

5. A cell comprising the nucleic acid molecule of claim 1.

6. The cell of claim 5 wherein said cell is a mammalian cell.

7. An expression vector comprising the nucleic acid molecule of claim 1.

8. A cell comprising the expression vector of claim 7.

9. The isolated nucleic acid molecule of claim 1 wherein said nucleic acid molecule encodes amino acid sequences including SEQ ID NO:7 and SEQ ID NO:10.

10. The isolated nucleic acid molecule of claim 1 wherein said nucleic acid is ribonucleic acid.

11. The isolated nucleic acid molecule of claim 10 wherein said ribonucleic acid is mRNA.

12. The isolated nucleic acid molecule of claim 1 wherein said nucleic acid molecule includes nucleic acid encoding a heavy chain of mammalian gamma-glutamylcysteine synthetase and nucleic acid encoding a light chain of mammalian gamma-glutamylcysteine synthetase.

13. The isolated nucleic acid molecule of claim 12 wherein said nucleic acid encoding said heavy chain has a nucleotide sequence as shown in SEQ ID NO:9.

14. The isolated nucleic acid molecule of claim 12 wherein said nucleic acid encoding said heavy chain encodes an amino acid sequence as shown in SEQ ID NO:10.

15. The isolated nucleic acid molecule of claim 12 wherein said nucleic acid encoding said light chain has a nucleotide sequence as shown in SEQ ID NO:6.

16. The isolated nucleic acid molecule of claim 12 wherein said nucleic acid encoding said light chain encodes an amino acid sequence as shown in SEQ ID NO:7.

17. An isolated nucleic acid molecule encoding a heavy chain of mammalian gamma-glutamylcysteine synthetase.

18. The isolated nucleic acid molecule of claim 17 wherein said nucleic acid is deoxyribonucleic acid.

19. The isolated nucleic acid molecule of claim 18 wherein said deoxyribonucleic acid is a cDNA.

20. The isolated nucleic acid molecule of claim 19 wherein said cDNA has a nucleotide sequence as shown in SEQ ID NO:9.

21. A cell comprising the nucleic acid molecule of claim 17.

22. The cell of claim 21 wherein said cell is a mammalian cell.

23. An expression vector comprising the nucleic acid molecule of claim 17.

24. A cell comprising the expression vector of claim 23.

25. The isolated nucleic acid molecule of claim 17 wherein said mammalian gamma-glutamylcysteine synthetase is rat gamma-glutamylcysteine synthetase.

26. The isolated nucleic acid molecule of claim 17 wherein said nucleic acid molecule encodes an amino acid sequence as shown in SEQ ID NO:10.

27. The isolated nucleic acid molecule of claim 17 wherein said nucleic acid is ribonucleic acid.

28. The isolated nucleic acid molecule of claim 27 wherein said ribonucleic acid is mRNA.

29. An isolated nucleic acid molecule encoding a light chain of mammalian gamma-glutamylcysteine synthetase.

30. The isolated nucleic acid molecule of claim 29 wherein said nucleic acid is deoxyribonucleic acid.

31. The isolated nucleic acid molecule of claim 30 wherein said deoxyribonucleic acid is a cDNA.

32. The isolated nucleic acid molecule of claim 31 wherein said cDNA has a nucleotide sequence as shown in SEQ ID NO:6.

33. A cell comprising the nucleic acid molecule of claim 29.

34. The cell of claim 33 wherein said cell is a mammalian cell.

35. An expression vector comprising the nucleic acid molecule of claim 29.

36. A cell comprising the expression vector of claim 35.

37. The isolated nucleic acid molecule of claim 29 wherein said mammalian gamma-glutamylcysteine synthetase is rat gamma-glutamylcysteine synthetase.

38. The isolated nucleic acid molecule of claim 29 wherein said nucleic acid molecule encodes an amino acid sequence as shown in SEQ ID NO:7.

39. The isolated nucleic acid molecule of claim 29 wherein said nucleic acid is ribonucleic acid.

40. The isolated nucleic acid molecule of claim 39 wherein said ribonucleic acid is mRNA.

* * * * *

UNITED STATES PATENT AND TRADEMARK OFFICE
CERTIFICATE OF CORRECTION

PATENT NO. : 5,747,329

DATED : May 5, 1999

INVENTOR(S) : Meister et al.

It is certified that error appears in the above-identified patent and that said Letters Patent is hereby corrected as shown below:

On the title page: Item [75]

Please add to [75] Inventors: Ning Yan, Plainsboro, New Jersey.

Signed and Sealed this

Fourth Day of January, 2000

*Attest:*

*Attesting Officer*     *Acting Commissioner of Patents and Trademarks*